US010330817B2

United States Patent
Bordakov et al.

(10) Patent No.: US 10,330,817 B2
(45) Date of Patent: Jun. 25, 2019

(54) PETROPHYSICALLY-REGULARIZED NUCLEAR MAGNETIC RESONANCE INVERSION

(71) Applicant: Schlumberger Technology Corporation, Sugar Land, TX (US)

(72) Inventors: George A. Bordakov, Richmond, TX (US); David F. Allen, Katy, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 307 days.

(21) Appl. No.: 14/993,957

(22) Filed: Jan. 12, 2016

(65) Prior Publication Data
US 2017/0003412 A1    Jan. 5, 2017

Related U.S. Application Data

(60) Provisional application No. 62/102,882, filed on Jan. 13, 2015.

(51) Int. Cl.
| | |
|---|---|
| *G01V 3/32* | (2006.01) |
| *G01V 3/14* | (2006.01) |
| *G01N 24/08* | (2006.01) |
| *G01R 33/44* | (2006.01) |
| *E21B 47/00* | (2012.01) |
| *G01V 3/38* | (2006.01) |
| *E21B 43/14* | (2006.01) |
| *E21B 43/26* | (2006.01) |
| *G01N 15/08* | (2006.01) |

(52) U.S. Cl.
CPC .............. *G01V 3/32* (2013.01); *E21B 47/00* (2013.01); *G01N 24/081* (2013.01); *G01R 33/448* (2013.01); *G01V 3/14* (2013.01); *G01V 3/38* (2013.01); *E21B 43/14* (2013.01); *E21B 43/26* (2013.01); *G01N 15/088* (2013.01)

(58) Field of Classification Search
None
See application file for complete search history.

(56) References Cited

U.S. PATENT DOCUMENTS

| | | | |
|---|---|---|---|
| 7,538,547 B2 | 5/2009 | Heaton | |
| 2008/0154509 A1* | 6/2008 | Heaton | ............ G01V 3/32 702/7 |
| 2012/0074934 A1 | 3/2012 | Green | |

(Continued)

FOREIGN PATENT DOCUMENTS

WO    2013184404 A1    12/2013

OTHER PUBLICATIONS

International Search Report issued in related PCT application PCT/US2016/013132 dated Apr. 4, 2016, 3 pages.

(Continued)

*Primary Examiner* — Kenneth Parker
*Assistant Examiner* — Steven B Gauthier

(57) ABSTRACT

A method for generating a porosity log for a reservoir in an organic shale. The method includes receiving data representing one or more parameters in a reservoir in an organic shale. At least one of the parameters includes porosity. By stochastically inverting the data, a distribution of porobodon features is estimated that matches an observed pulse decay curve. The porosity data relates to petrophysical restrictions on at least one of the porobodon features.

19 Claims, 9 Drawing Sheets

(56) References Cited

U.S. PATENT DOCUMENTS

2012/0273193 A1    11/2012   Sen et al.
2013/0200890 A1*   8/2013   Hursan ................ G01V 3/32
                                                                     324/303
2014/0285190 A1*   9/2014   Allen ................... G01V 3/32
                                                                     324/303

OTHER PUBLICATIONS

Clerke, et al. "Application of Thomeer Hyperbolas to decode the pore systems, facies and reservoir properties of the Upper Jurassic Arab D Limestone, Ghawar field, Saudi Arabia: A "Rosetta Stone" approach", GeoArabia, 2008, vol. 13, No. 4, pp. 113-160.

Clerke, et al. "Wireline Spectral Porosity Analysis of the Arab Limestone—From Rosetta Stone to Cipher", SPWLA 55th Annual Logging Symposium, May 18-22, 2014, Abu Dhabi, UAE, SPWLA-2014-D, pp. 1-23.

Jain, et al. "Characterization of Underlying Pore and Fluid Structure Using Factor Analysis on NMR Data", SPWLA 54th Annual Symposium in New Orleans, Louisiana, Jun. 22-26, 2013, SPWLA-2013-TT, pp. 1-16.

Rylander, et al. "NMR T2 Distributions in the Eagle Ford Shale: Reflections on Pore Size", SPE Unconventional Resources Conference—USA, Apr. 10-12, 2013, The Woodlands, Texas, USA, SPE-164554-MS, pp. 1-15.

Prange, et al. "Understanding NMR T2 spectral uncertainty", Journal of Magnetic Resonance, vol. 204, 2010, pp. 118-123.

Price, et al. "Differential Evolution. A Practical Approach to Global Optimization," Chapter 2—The Differential Evolution Algorithm. Springer-Verlag, Berlin, Heidelberg, 2005, pp. 37-134.

Reeder, et al. "A Multimeasurement Core-Log Integration for Advanced Formation Evaluation of Oil Shale Formations: A Green River Formation Case Study", Petrophysics, Jun. 2013, vol. 54, No. 3, pp. 258-273.

* cited by examiner

PETROPHYSICALLY-REGULARIZED NUCLEAR MAGNETIC RESONANCE INVERSION

CROSS-REFERENCE TO RELATED APPLICATIONS

This application claims benefit of U.S. Provisional Patent Application Ser. No. 62/102,882, filed Jan. 13, 2015, which is herein incorporated by reference.

BACKGROUND

The present disclosure relates generally to petrophysically-regularized nuclear magnetic resonance inversion and, more particularly, to petrophysically-regularized nuclear magnetic resonance inversion in the time domain using a porosity input for unconventional reservoirs in organic shales.

The focus of petroleum industry activity in North America in the last 3 to 4 years has migrated from gas shale to liquid (e.g., oil producing) shale. There are differences in the properties of the liquid hydrocarbon phase versus the gaseous hydrocarbon phase and, thus, differences in the resulting interactions between the fluids and the rock matrix. Therefore, production and evaluation models developed for gas may not be directly applicable to oil.

Production of oil from organic shale reservoirs is a combination of two major factors: reservoir quality and completions quality. Reservoir quality is a function of porosity, hydrocarbon saturation, pore pressure, and matrix permeability, while completions quality is a function of hydraulic fracture surface area and fracture conductivity. Hydraulic fracture surface area, porosity, saturations of various fluids, and pore pressure dominate initial production rates. However, to sustain production later in the time matrix, permeability becomes increasingly relevant. The permeability of oil from organic shale is believed to be a function of pore throat size, wettability, and water saturation, which is the same as a conventional reservoir. Nuclear magnetic resonance ("NMR") logging is the primary method in the industry to characterize these reservoir parameters, and it has recently been used for unconventional reservoirs in organic shale.

One proposed technique for pore partitioning in carbonates with NMR logs is guided by mercury injection capillary pressure test ("MICP") data. This technique has subsequently been developed into CIPHER$^{SM}$—a petrophysically regularized time domain NMR inversion—that has demonstrated success in a blind field test with data from Arab limestone. The method used in CIPHER$^{SM}$ is decomposition of NMR T2 distribution into a number of Gaussian components. These Gaussian components obtained from the T2 distribution are attributed to different porobodons. The term "porobodon" postulates the relationship between the NMR relaxation time spectrum and porositon, which in turn is a distinct and separable distribution in maximum pore throat diameters space. CIPHER$^{SM}$ performs stochastic inversion in the space of pulse decay curves based on a porobodon/porositon approach with petrophysical restrictions. It overcomes problems with the biased commercial NMR T2 distribution and provides uncertainty estimates for the inversion results. These uncertainty estimates are used to determine the petrophysical restriction mentioned above. However CIPHER$^{SM}$ does not include total porosity information as a factor guiding inversion.

A challenge for NMR based reservoir characterization in organic shale is low sensitivity of NMR logs to the short time part of NMR relaxation time distribution, particularly in the range of T2 below about 0.2-0.3 ms. The low sensitivity leads to the deficit in log T2 distributions versus the core in short ranges as well to total porosity deficit in NMR versus the core. It is the short T2 part in the oil bound in the organic shale that is exposed; hence, the whole NMR applicability for reservoir characterization becomes questionable. Improving a signal and/or noise ratio for the first echo and reducing echo spacing alleviates the challenge, but these are quite daunting hardware design tasks. CIPHER$^{SM}$ has demonstrated success in overcoming similar low sensitivity challenges for long relaxation times with existing hardware. Therefore, a similar technique may be applied for unconventional reservoirs in organic shale.

SUMMARY

A summary of certain embodiments disclosed herein is set forth below. It should be understood that these aspects are presented merely to provide the reader with a brief summary of certain embodiments and that these aspects are not intended to limit the scope of this disclosure. Indeed, this disclosure may encompass a variety of aspects that may not be set forth in this section.

Systems, methods, and computer-readable media for generating a porosity log for a reservoir in an organic shale are disclosed. Data is received representing one or more parameters in a reservoir in an organic shale. At least one of the parameters includes porosity. By stochastically inverting the data, a distribution of porobodon features is estimated that matches an observed pulse decay curve. The porosity data relates to petrophysical restrictions on at least one of the porobodon features.

The brief summary presented above is intended to familiarize the reader with certain aspects and contexts of embodiments of the present disclosure without limitation to the claimed subject matter.

DETAILED DESCRIPTION

Figure 1:
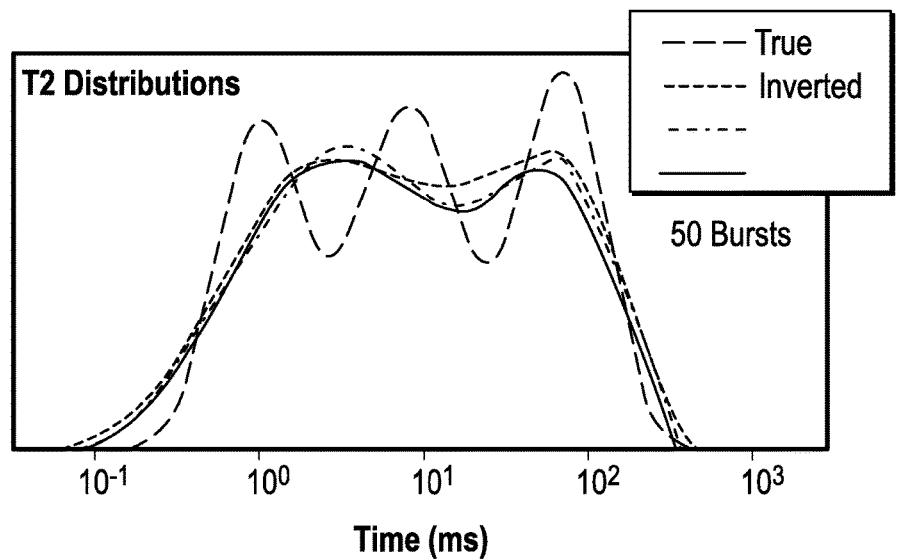
FIG. 1 depicts a graph showing 50 EPM bursts in 1 ms, according to an embodiment.

One or more specific embodiments of the present disclosure are described below. These embodiments are merely examples of the presently disclosed techniques. Additionally, in an effort to provide a concise description of these embodiments, all features of an actual implementation may not be described in the specification. It should be appreciated that in the development of any such implementation, as in any engineering or design project, numerous implementation-specific decisions are made to achieve the developers' specific goals, such as compliance with system-related and business-related constraints, which may vary from one implementation to another. Moreover, it should be appreciated that such development efforts might be complex and time consuming, but would nonetheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The embodiments discussed below are intended to be examples that are illustrative in nature and should not be construed to mean that the specific embodiments described herein are necessarily preferential in nature. Additionally, it should be understood that references to "one embodiment" or "an embodiment" within the present disclosure are not to be interpreted as excluding the existence of additional embodiments that also incorporate the recited features.

Incorporating total or aggregate porosity information into the CIPHER$^{SM}$ time domain using stochastic inversion allows modified inversion to be capable of overcoming a short T2 challenge even without using the first echo. This may allow high quality total porosity logs to be obtained in organic shale from elemental capture spectroscopy ("ECS") data. This data, together with NMR data, may improve the characterization of (1) porosity partition occupied by short relaxation times and of (2) the mean time value in that range. That data may also be used to evaluate matrix permeability characteristics.

The systems and methods disclosed herein are based on the porobodon/porositon approach (i.e., distinct and separable distribution components in NMR relaxation time space match distribution components in maximum pore throat diameters space). In addition, the systems and methods disclosed herein include two parts. First, stochastic inversion may be used to estimate a porobodon feature distribution that matches the observed pulse decay curves and total porosity logs involving petrophysical restrictions on these porobodon features. Then, petrophysical restrictions may be determined based on the above-mentioned inversion results combined with data from other logs and core.

Stochastic Inversion

Following the porobodon/porositon approach, NMR relaxation time distributions may be presented as a sum of Gaussian components in a discretized logarithmic time space:

$$\log(T_{2j}) = \log(T_{2min}) + \left(\frac{j-1}{NT_2 - 1}\right) \times [\log(T_{2max}) - \log(T_{2min})], \quad (1)$$

$$amp_j = \sum_{k=1,\ldots NG} a_k \exp\left[-\left(\frac{j - m_k}{\sigma_k}\right)^2\right], \quad j = 1, \ldots NT_2 \quad (2)$$

In equation, (1) $NT_2$ is a number of discrete T2 bins, which are spaced equally logarithmically between the selected minimum $T_{2min}$ and maximum $T_{2max}$. $amp_j$ and $T_{2j}$ are amplitude and T2 relaxation time, respectively, of the component $j=1, \ldots NT_2$. NG is a number of porobodons. The variables in equation (2) represent porobodon parameters. For example, $a_k$ represents the porobodon amplitudes, $m_k$ represents the porobodon positions, and $\sigma_k$ represents the porobodon widths. Equations (1) and (2) are written for T2 while similar equations can also be specified for T1 and diffusion.

Echoes (e.g., $\overline{echo_i}$) are pulse decay curves and can be reconstructed from the amplitudes as follows:

$$\overline{echo_i} = \sum_{j=1,\ldots NT_2} P(T_{2j}, T_{12r}) K_{ij} amp_j, \quad i = NS, \ldots NE \quad (3)$$

In equation (3), $K_{ij}$ is the NMR kernel matrix, $P(T_{2j}, T_{12r})$ is the polarization correction term depending on T2 and T1/T2 ratio $T_{12r}$, and i=NS, . . . NE are sequential echo numbers. By specifying kernel equations, equation (3) can be written for complete NMR echoes as well as for window sums of echoes both for main CPMG and bursts. Such equations can also be modified to accommodate diffusion by adjusting j in equations (1) and (2) with the diffusion term. Specific equations for kernel matrices and polarization correction terms are tool dependent.

Theoretically restored echoes (e.g., $\overline{echo_i}$) may be compared with measured NMR echoes (e.g., $echo_i$). The differences between the measured and restored echoes (e.g., $echo_i - \overline{echo_i}$) are assumed to be independent random variables with zero expected value and standard deviations $s_i$. Taking into consideration some other a priori data such as $s_i$, the probability distribution of $a_k$, $m_k$ and $\sigma_k$ matching the probability distribution of $echo_i - \overline{echo_i}$ may be estimated. In the process of this probability distribution inversion, $a_k$, $m_k$ and $\sigma_k$ may be considered to be restricted based on a priori knowledge. For example, $a_k$, $m_k$ and $\sigma_k$ may be as shown in equation (4) below:

$$0 \leq a_k \leq a_{kmax}$$

$$m_{kmin} \leq m_k \leq m_{kmax} \quad a_{kmax} \in \{0, +\infty\}, k=1, \ldots NG$$

$$\sigma_{kmin} \leq \sigma_k \leq \sigma_{kmax} \quad (4)$$

Restrictions of the type in equation (4) may be referred to as petrophysical restrictions. The meaning of the first restriction is that some porobodons are included in the inversion with non-negativity constraints on the amplitude, and some are excluded. Also in addition to $a_k$, $m_k$ and $\sigma_k$, there are other variables of interest such as porobodon volumes (e.g., $V_k = \sqrt{\pi} a_k \sigma_k$). The sum of these porobodon volumes (e.g., $\Sigma_{k=1, \ldots NG} V_k$) may be compared to the total porosity $\phi$. Namely, the differences between the sum of the porobodon volumes and the input total porosity (e.g., $\phi - \Sigma_{k=1, \ldots NG} \sqrt{\pi} a_k \sigma_k$) are assumed to be random variables with zero expected value and standard deviations $s_\phi$ independent of $echo_i - \overline{echo_i}$.

There are various methods that can be used to estimate the probability distribution of $a_k$, $m_k$ and $\sigma_k$ given equation (4) (or some other derived variables like $V_k$). In one embodiment, Bayesian methods may be used. Any method capable of producing quantiles (e.g., P10, P50, P90) and modes of $V_k$, $m_k$ and $\sigma_k$ together with quality control criteria of the inversion itself may be used to pick up petrophysical restrictions.

In one embodiment, a heuristic method based on a differential evolution stochastic optimization algorithm may be used. It may be assumed that mismatches between measured and restored echoes, as well as measured and restored total porosity, are normally distributed with known standard deviation $echo_i - \overline{echo}_i \sim N(0, s_i)$, $\phi - \Sigma_{k=1, \ldots NG} \sqrt{\pi} a_k \sigma_k \sim N(0, s_\phi)$. The combined weighted normalized mismatch $\Delta$ may be defined to be minimized by a differential evolution method as shown in equation (5) below:

$$D = (1-\alpha) \frac{\Sigma_{\forall i} w_i \left( \frac{echo_i - \overline{echo}_i}{s_i} \right)^2}{\Sigma_{\forall i} w_i} + \left( \frac{\phi - \sum_{k=1,\ldots NG} \sqrt{\pi} a_k \sigma_k}{s_\phi} \right)^2 \quad (5)$$

$$w_i \geq 0, \; 1 > \alpha > 0$$

Independent estimates may be obtained of standard deviations $s_i$, $s_\phi$. For NMR, $s_i$ may be estimated from measurement noise derived from a "minus" signal obtained from phase alternated pairs sequences, and $s_\phi$ for total porosity can either be a known tool measurement property or estimated by inversion that delivers $\phi$ from known tool properties. However, while $s_i$, $s_\phi$ may not be known, knowledge of their values relative to each other may be sufficient. Expectation of D, according to equation (5), is equal to 1. If $s_i = k_i s$, $s_\phi = k_\phi s$, and $k_i$, $k_\phi$ are known, $s_i$ may be substituted with $k_i$, and $s_\phi$ may be substituted with $k_\phi$ in equation (5). Then, the expectation of D may be equal to $s^2$. In addition, distributions of $echo_i - \overline{echo}_i$, $\phi - \Sigma_{k=1, \ldots NG} \sqrt{\pi} a_k \sigma_k$ may not be normal as soon as they are independent, as these distributions have zero expectation, and their number of i is big enough so the central limit theorem applies (e.g., for practical purposes, the number should be about 50 or more).

Various weights $w_i$ may be assigned to echoes or window sums. For example, burst weights may be increased compared to the main CPMG. Additionally, the coefficient $\alpha$ may control the weight of total porosity data with respect to NMR. In case no a priori information exists about relative certainty of porosity data versus NMR, $\alpha = \frac{1}{2}$ may be selected. This choice may be adjusted based on the expectations of the data with increasing $\alpha$ corresponding to increasing relative certainty of the total porosity. In addition, in the case of a certain total porosity data, the data may come in the form of a restriction rather than in the form of a cost function term. In other words, equation (5) may take form of:

$$D = \frac{\Sigma_{\forall i} w_i \left( \frac{echo_i - \overline{echo}_i}{s_i} \right)^2}{\Sigma_{\forall i} w_i} \quad (6)$$

$$w_i \geq 0$$

$$\phi = \sum_{k=1,\ldots NG} \sqrt{\pi} a_k \sigma_k$$

The case of $\alpha = 0$ represents the CIPHER$^{SM}$ time domain inversion. Differential evolution minimization procedures may maintain a population of $a_k$, $m_k$, $\sigma_k$ samples which, upon convergence, may be used to sample the probability distribution of $V_k$, $m_k$, $\sigma_k$ and estimate quantiles and modes that may be used for further analysis. As such, differential evolution stopping criteria may be designed so the population converges "just enough." First, a high degree of convergence may be used to obtain an estimate $s_E^2$ of the expectation of the normalized mismatch E(D). The stopping criteria at the first stage may be designed based on the hypothesis testing criteria calculated from the spread of D in the population. A low significance level (i.e., a high confidence level) which is defined as "one-minus significance level," may be used at this stage. Upon determining $s_E^2$, another minimization procedure may be run with relaxed significance level(s) to sample the area of D around $s_E^2$. Stopping criteria may be designed similarly to one at the first stage but with different significance levels.

Once the population of $a_k$, $m_k$, $\sigma_k$ is converged to what is considered a desired sample of distributions, quantiles and modes ("best fits") of $a_k$, $m_k$, $\sigma_k$ may be estimated from the population. Quality criteria of the inversion $\Delta = (s_E^2/s^2 - 1)/\sqrt{0.5 + 0.5/Card(\forall i)}$ may include a confidence level $p_c$ reached at the first minimization procedure (estimating E(D)). Quality criteria may also include qualitative "yes/no" criteria showing whether confidence levels were reached at a subsequent minimization procedure (e.g., sampling the distribution). Quality criteria may further include whether independent estimations of misfit $s^2$ are available (e.g., from NMR noise estimation and tool properties for total porosity measurement), or whether differences $\Delta$ exist between $s_E^2$ and $s^2$ normalized by the theoretical standard deviation of D (e.g., in case of equal weights $w_i$ in (4) $\Delta = (s_E^2/s^2 - 1)/\sqrt{2\alpha^2 + 2(1-\alpha)^2/Card(\forall i)}$, where the Card($\forall i$) is total number of NMR echoes or windows sums participating in the inversion). Quality control criteria may further include positions of $m_k$, $\sigma_k$ best fits relative to the boundaries of the restrictions in equation (4), which should be positioned away from restriction boundaries. Quality control criteria may yet further include percentile values of $m_k$, $\sigma_k$ best fits which should not be close to 0% or 100% (e.g., from about 10% to about 90% or about 20% to about 80%). Inversion results with satisfactory quality criteria: high enough $p_c$ (e.g., at least 95%), "yes" convergence for the second stage minimization, and low enough $\Delta$ (e.g., less than 3) can be used as porosity partitioning results (i.e., porobodon volumes, positions, and widths). They may also be used to determine petrophysical restrictions in equation (4) as described below.

Determining Proper Petrophysical Restrictions

A priori knowledge about the presence of porobodons in some zones of the logs may be used to determine the petrophysical restrictions in zones which are then applied for the whole log. The number of porobodons to seek is determined based on knowledge of the core, logs, and NMR sensitivity. For this purpose, core NMR or core MICP data may be used. For example, core NMR T2 distributions in combination with log NMR T2 distributions suggest 2 porobodons or 3 porobodons, with porobodons corresponding to the T2 interval 2-20 ms overlapping each other. In another embodiment, exploratory factor analysis of commercial NMR T2 distributions may be used for this purpose.

Then, zones may be defined where a subset of the total porobodon sets are present. It can be either one porobodon or more provided they are clearly separated in T2 space so commercial T2 inversion gives T2 distributions with clear visible separation of porobodons or such zones are identified by factor analysis. Identification of such zones is done based on discriminator logs whose values are in the interval(s) specified by a user. The discriminator logs are any which are sensitive to the porosity partitioning and may include commercial T2 distribution bins as well as bound fluid volume and log mean T2 obtained from it, volumes of commercial NMR T2 distributions factors, porosity (e.g., total NMR, individual NMR bins, neutron, total, etc.), elemental weight fractions or mineral volume fractions provided by nuclear measurements or values derived from them (e.g., carbon weight or total organic content (TOC)), NMR first echo amplitude, depth (e.g., just to represent overall analyst judgment), a combination thereof, or the like.

Each of the echoes in a zone satisfying specified discriminators is stacked and then both commercial and stochastic inversion is performed for stacked echoes. Commercial inversion of stacked echoes may be substituted with stacking commercial inversions of individual echoes if the echoes are close enough to each other. Restrictions, as included in equation (4) for the distribution of $a_k$, are picked based on the knowledge of the porobodons that are present. Restrictions for $m_k$ and $\sigma_k$ are picked as wide as physically meaningful and/or as wide as commercial T2 distribution allows, if there are several distinct porobodons that are involved. P10, P50, and P90 quantiles best fits (modes) for porobodon volumes, position, and widths are presented together with measured stacked echoes, echoes restored stochastic inversion best fit, and echoes restored from commercial T2.

For visual quality control, a "worm" representing a window averaging result of measured stacked echoes over time may be presented as well. Visual comparison of the "worm" with restored echoes is used instead of, or in addition to, a normalized misfit mismatch Δ for quality control of the inversion convergence and quality of the restrictions.

Inversion may be performed interactively with the restriction on position and width of the selected porobodon being selected as wide as possible until quality control criteria both visual (e.g., comparison restored echoes with "worm" and stochastic inversion T2 distribution with commercial one) and numerical are satisfied. Once satisfactory inversion results are obtained, P10 and P90 quantiles of the porobodon positions and widths are used as restriction boundaries for the porobodons in further analyses. Next, a zone may be identified where one new porobodon, in addition to the porobodons for which restrictions are already defined, is substantially present. In another embodiment, a zone may be identified where more than one porobodon is present, if these new porobodons are clearly distinct on commercial T2 distributions. Stacking and inversion, as described above, may be performed as well. Restrictions for new porobodons are selected as wide as possible until permitted by quality control criteria. P10 and P90 quantiles may again be used in further analyses as restriction boundaries of these new porobodon positions and widths.

The restriction determination process described above may be iteratively performed until each of the restrictions for the porobodon positions and widths are defined. The procedure described above modifies inversion using total porosity as per equations (5) or (6), uses the results of exploratory factor analysis of commercial T2 distributions to determine the number of porobodons and restrictions on them, and uses different nuclear measurements based on elemental weight fractions or mineral volume fractions or their derivatives such as carbon or TOC.

In addition, the restrictions as per equation (4) can be selected directly, and core NMR or core NMR echo trains can be used in the procedure described above instead of, or in addition to, stacked NMR log echo trains. In another embodiment, the restrictions as per equation (4) can be selected to mimic the shape of the factors resulting from exploratory factor analysis of NMR logs T2 distributions or core NMR T2 distributions.

Comparison of New Inversion Results Versus Existing CIPHER$^{SM}$ and NMR Bin Porosity Synthetic data is used to compare results of the proposed inversion versus CIPHER$^{SM}$ and a conventional NMR bin porosity analysis. The synthetic data contains 3 porobodons with the properties as described in the following table:

TABLE 1

| Short | | Middle | | Long | |
|---|---|---|---|---|---|
| Volume | Width (dec) | Volume | Width (dec) | Volume | Width (dec) |
| 0.06 | 0.602 | 0.08 | 0.758 | 0.07 | 0.602 |

In Table 1, width (dec) $W_k = 2\sigma_k \log(T_{2max}/T_{2min}) \sqrt{\log 2}/((NT_2-1)\log 10)$ is a bin-independent equivalent of $\sigma_k$, and volume is $V_k = \sqrt{\pi} a_k \sigma_k$. Width (dec) $W_k$ is the distance between positions, and the distribution value is equal to the half of the value in the position of the mean with one such position being located at T2 shorter than mean T2 and one being located at T2 longer than mean T2. The width is defined in decades (e.g., it is 10 times the absolute value of the decadic logarithm of the ratio of the corresponding T2).

Several synthetic datasets have been created with these porobodons. The difference between the datasets may be seen in the mean T2 positions of the porobodons and acquisition parameters. These mean T2 positions $TM_k = T_{2min}(T_{2max}/T_{2min})^{(m_k-1)/(NT_2-1)}$ that are bin-independent equivalents of $m_k$ are presented in Table 2 below together with the number of echoes in the main CPMG and the number of EPM bursts (each EPM has 30 echoes).

TABLE 2

| Case Name | Short Mean T2 (ms) | Middle Mean T2 (ms) | Long Mean T2 (ms) | Echoes/ Bursts |
|---|---|---|---|---|
| 1 ms 50 Bursts | 1.0 | 8.0 | 70.0 | 1800/50 |
| 1 ms 10 Bursts | 1.0 | 8.0 | 70.0 | 3000/10 |
| 0.5 ms 50 Bursts | 0.5 | 4.0 | 35.0 | 1800/50 |
| 0.5 ms 10 Bursts | 0.5 | 4.0 | 35.0 | 3000/10 |
| 0.25 ms 50 Bursts | 0.25 | 2.0 | 17.5 | 1800/50 |
| 0.25 ms 10 Bursts | 0.25 | 2.0 | 17.5 | 3000/10 |
| 0.1 ms 50 Bursts | 0.1 | 0.8 | 0.7 | 1800/50 |
| 0.1 ms 10 Bursts | 0.1 | 0.8 | 0.7 | 3000/10 |

The first 80 traces of each dataset contain short porobodons. The next 80 traces contain middle porobodons. The next 80 traces contain long porobodons. The last 80 traces contain the sum of the 3 porobodons. Echo trains for each of these traces are modeled for the CMRB tool with 0.2 ms echo spacing, zero diffusion, a constant T1/T2 ratio of 1.5, and normal uncorrelated noise of 0.0209 per-echo amplitude. Modeled echo trains are stacked with level 3 (e.g., while not stacking across changes in porobodon composition) and processed with commercial CMR T2 inversion with the settings of automatic regularization, constant T1/T2 ratio of 1.5, and start echo 1.

Figure 2:
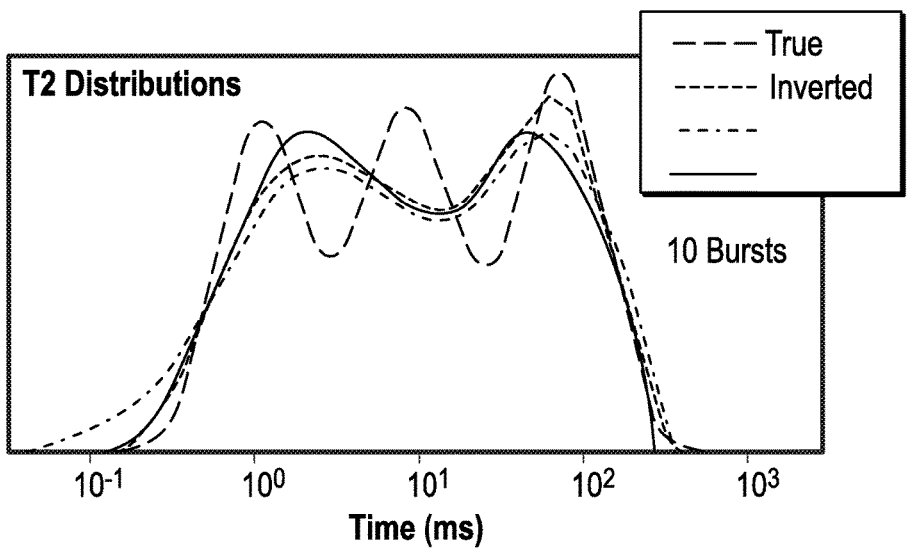
FIG. 2 depicts a graph showing 10 EPM bursts in 1 ms, according to an embodiment.
Figure 3:
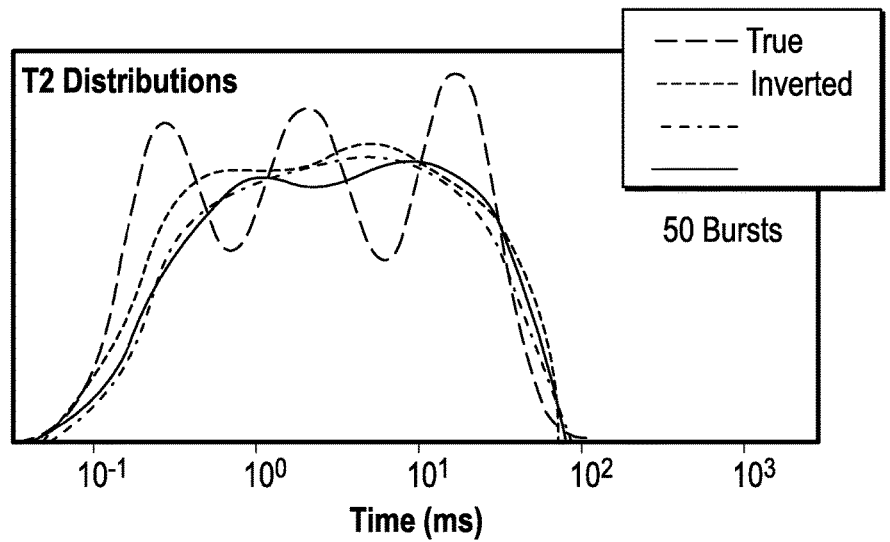
FIG. 3 depicts a graph showing 50 EPM bursts in 0.5 ms, according to an embodiment.
Figure 4:
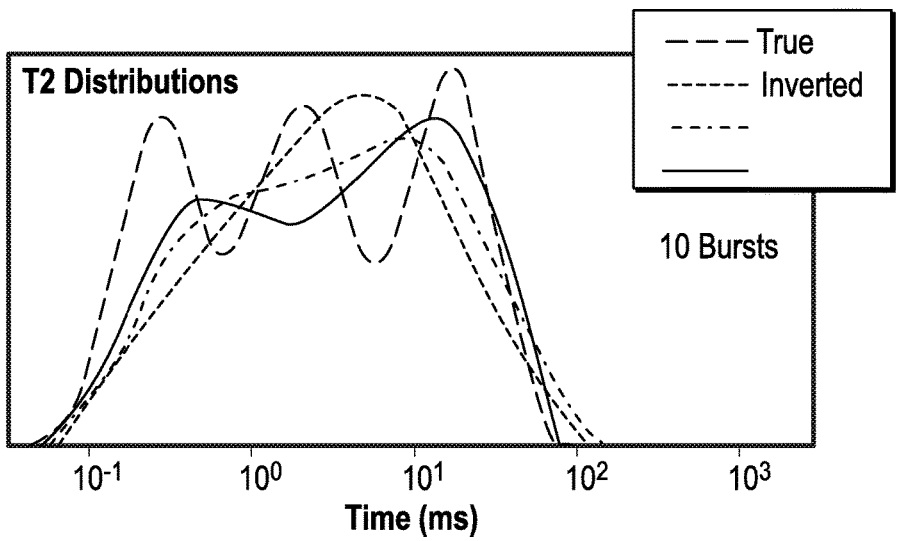
FIG. 4 depicts a graph showing 10 EPM bursts in 0.5 ms, according to an embodiment.
Figure 5:
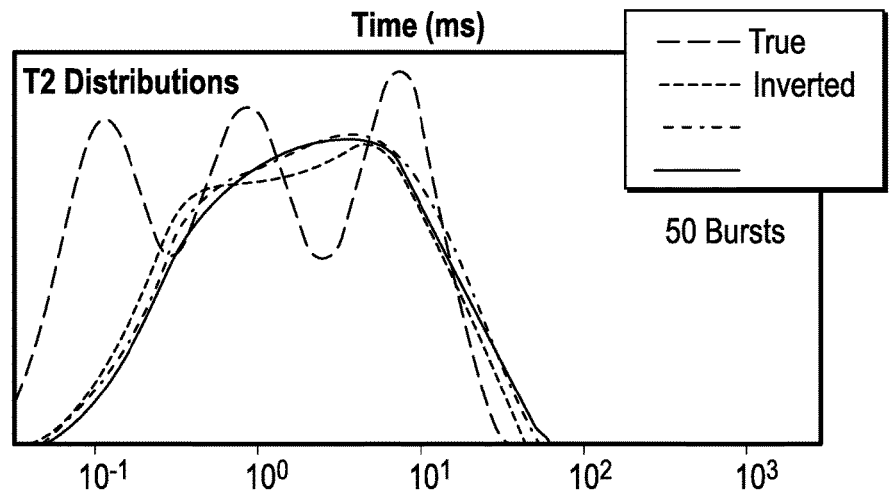
FIG. 5 depicts a graph showing 50 EPM bursts 0.25 ms, according to an embodiment.
Figure 6:
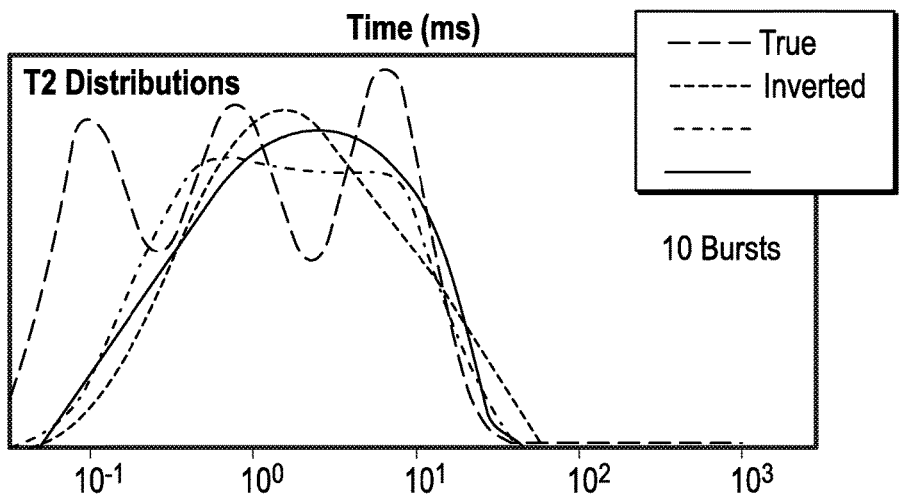
FIG. 6 depicts a graph showing 10 EPM bursts in 0.25 ms, according to an embodiment.

Commercial CMR T2 inversion for 3 randomly picked traces with the sum of the 3 porobodons versus true model T2 distribution for various cases are shown in the figures. More particularly, FIG. 1 depicts a graph showing 50 EPM bursts in 1 ms. FIG. 2 depicts a graph showing 10 EPM bursts in 1 ms. FIG. 3 depicts a graph showing 50 EPM bursts in 0.5 ms. FIG. 4 depicts a graph showing 10 EPM bursts in 0.5 ms. FIG. 5 depicts a graph showing 50 EPM bursts 0.25 ms. FIG. 6 depicts a graph showing 10 EPM bursts in 0.25 ms.

The commercial T2 inversion makes individual porobodon T2 distributions almost indistinguishable and may lose sensitivity at the 0.1 ms T2 range. This synthetic data is analyzed with CIPHER$^{SM}$ and with modified inversion as described above. CIPHER$^{SM}$ and the inversion interactive procedure of finding restrictions (described above) are used. The new inversion interactive procedure may be used because it is known that 3*80 traces in each dataset contain one specific porobodon. The total porosity input $\phi$ for the modified inversion is 0.06+0.08+0.07=0.21. Values for $s_i$ are estimated from variances of modeled "minus" signals emulating phase alternated pairs sequences with per echo noise of 0.0209. A value for $s_\phi$ is taken as 0.0075, weights $w_i$ are equal to each other, and $\alpha=\frac{1}{2}$. Additionally, NMR bin porosity values are obtained from inverted T2 distributions with a cutoff selection made via observation of the first 3*80 traces in each dataset containing individual porobodons. Each of these results for specific cases are presented in the figures below.

Figure 7:
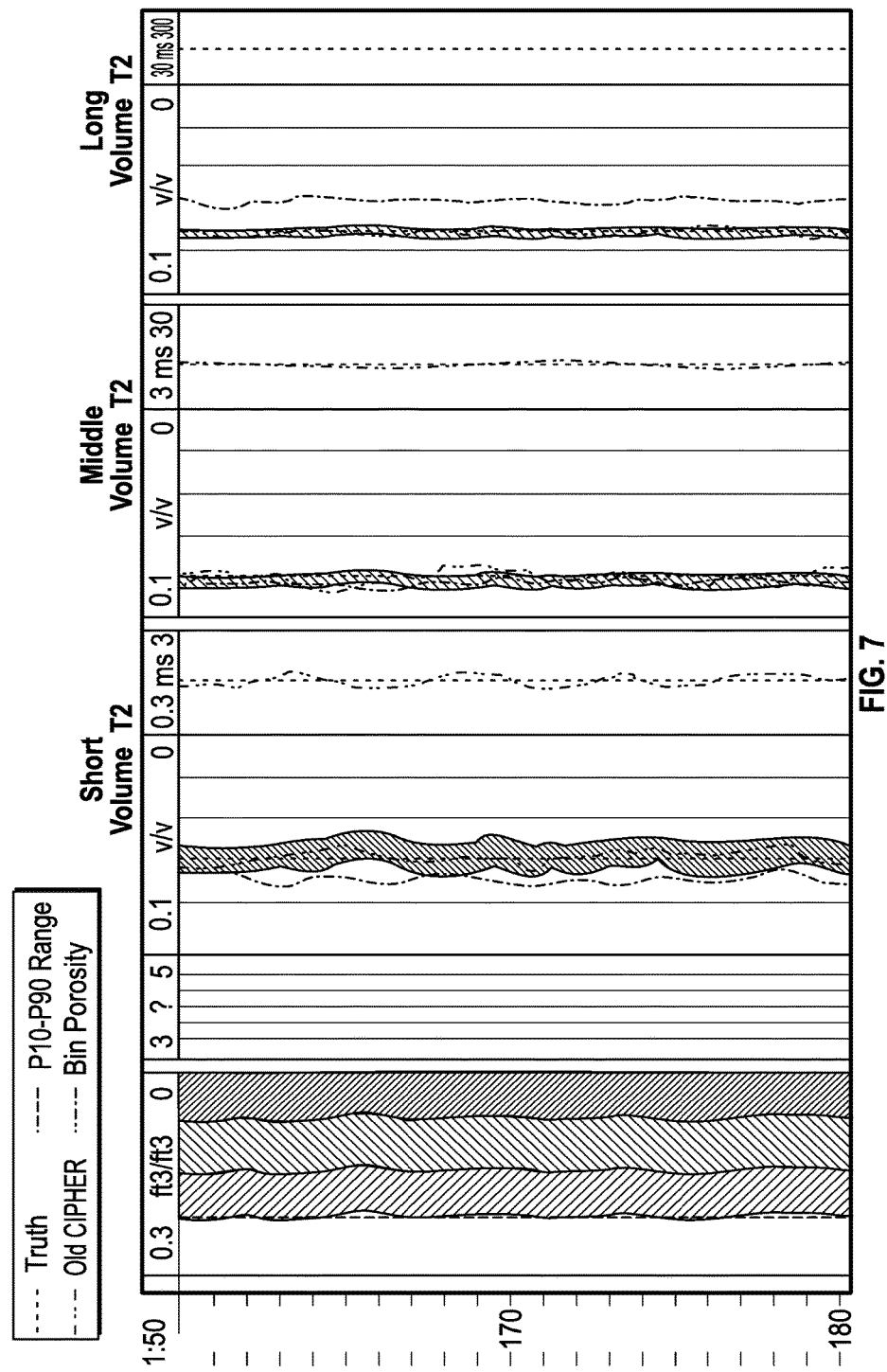
FIG. 7 depicts a graph showing a 1 ms short porobodon with 50 bursts, according to an embodiment.
Figure 8:
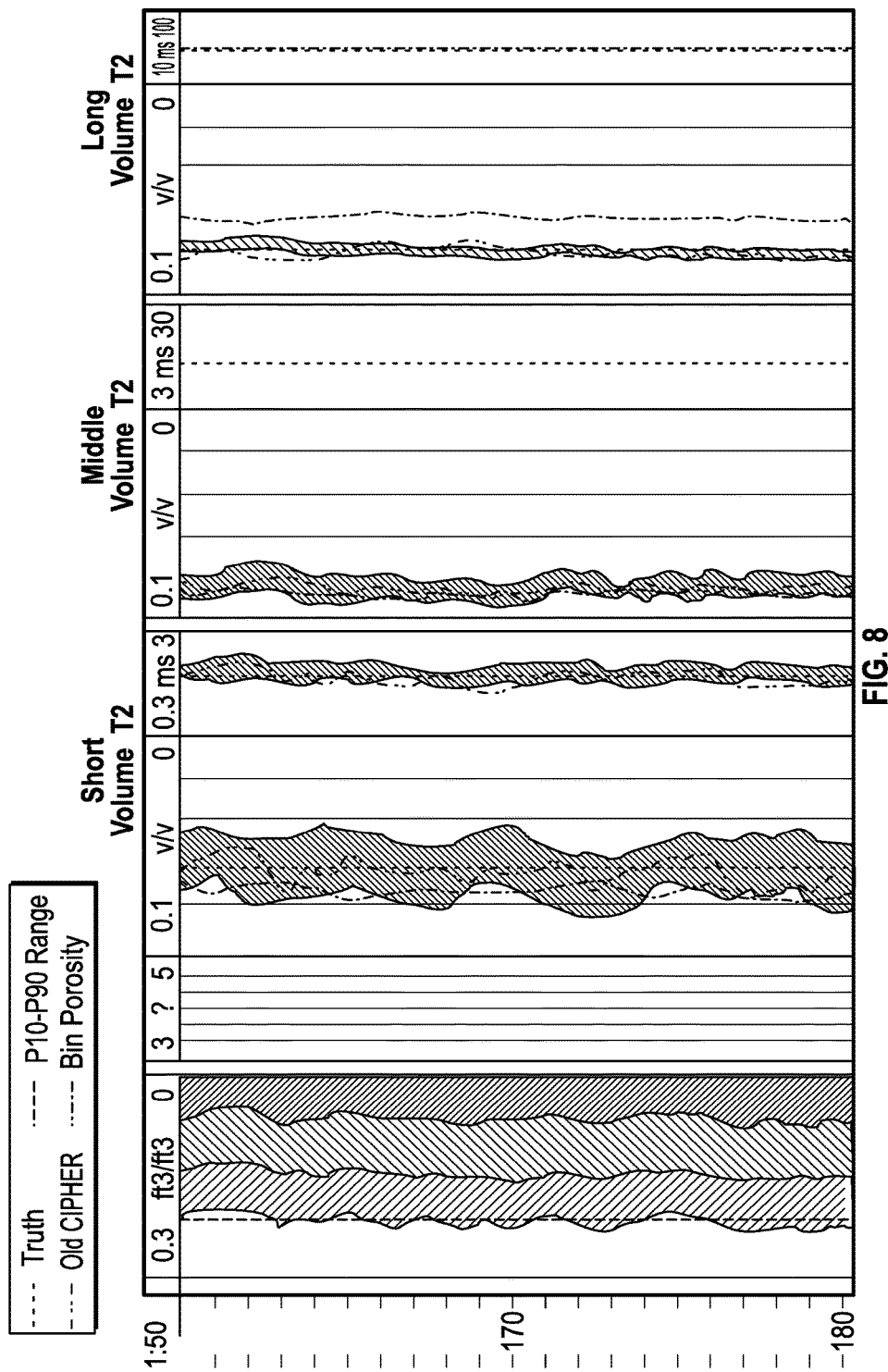
FIG. 8 depicts a graph showing a 0.5 ms short porobodon with 50 bursts, according to an embodiment.
Figure 9:
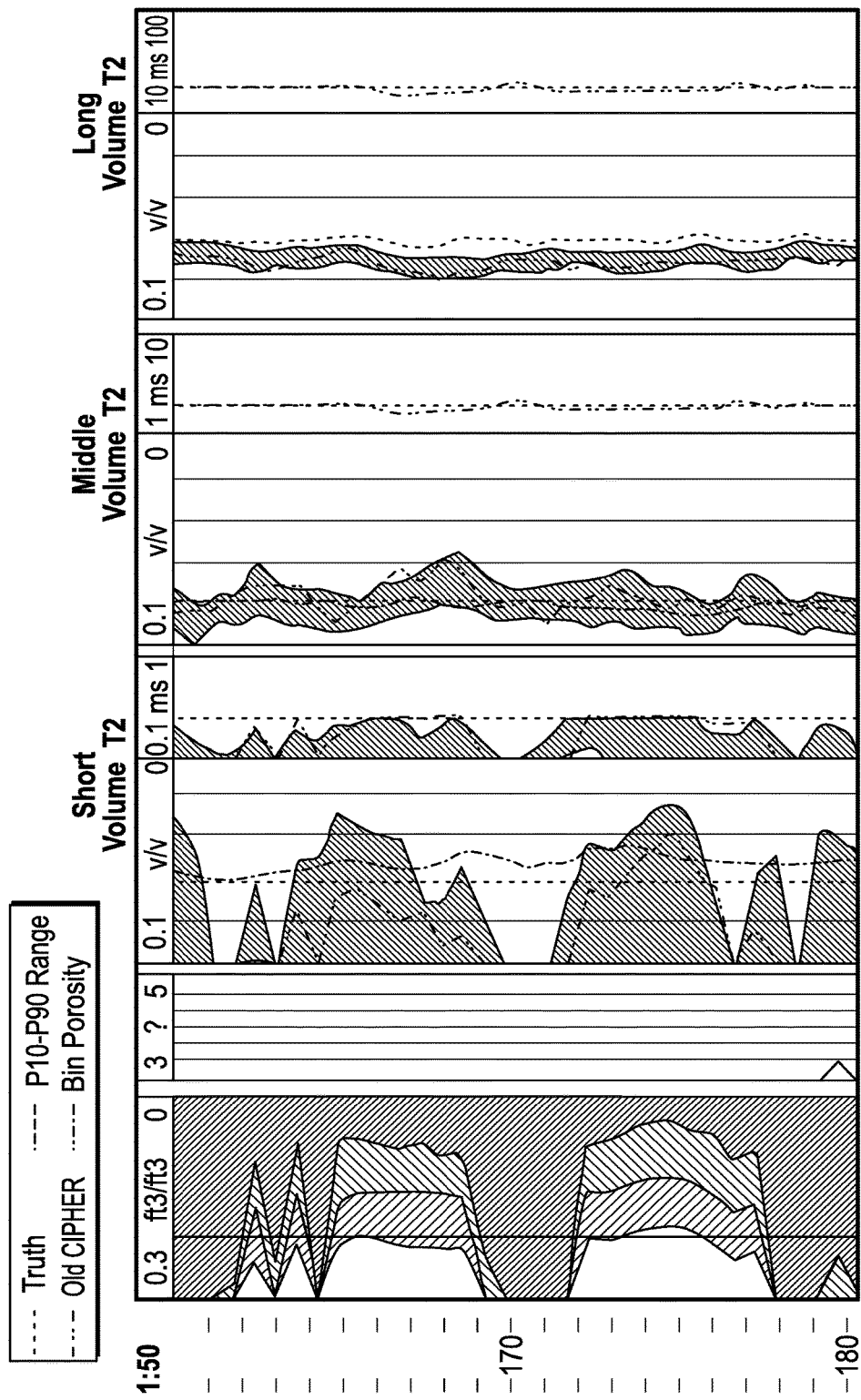
FIG. 9 depicts a graph showing a 0.25 ms short porobodon with 50 bursts, according to an embodiment.
Figure 10:
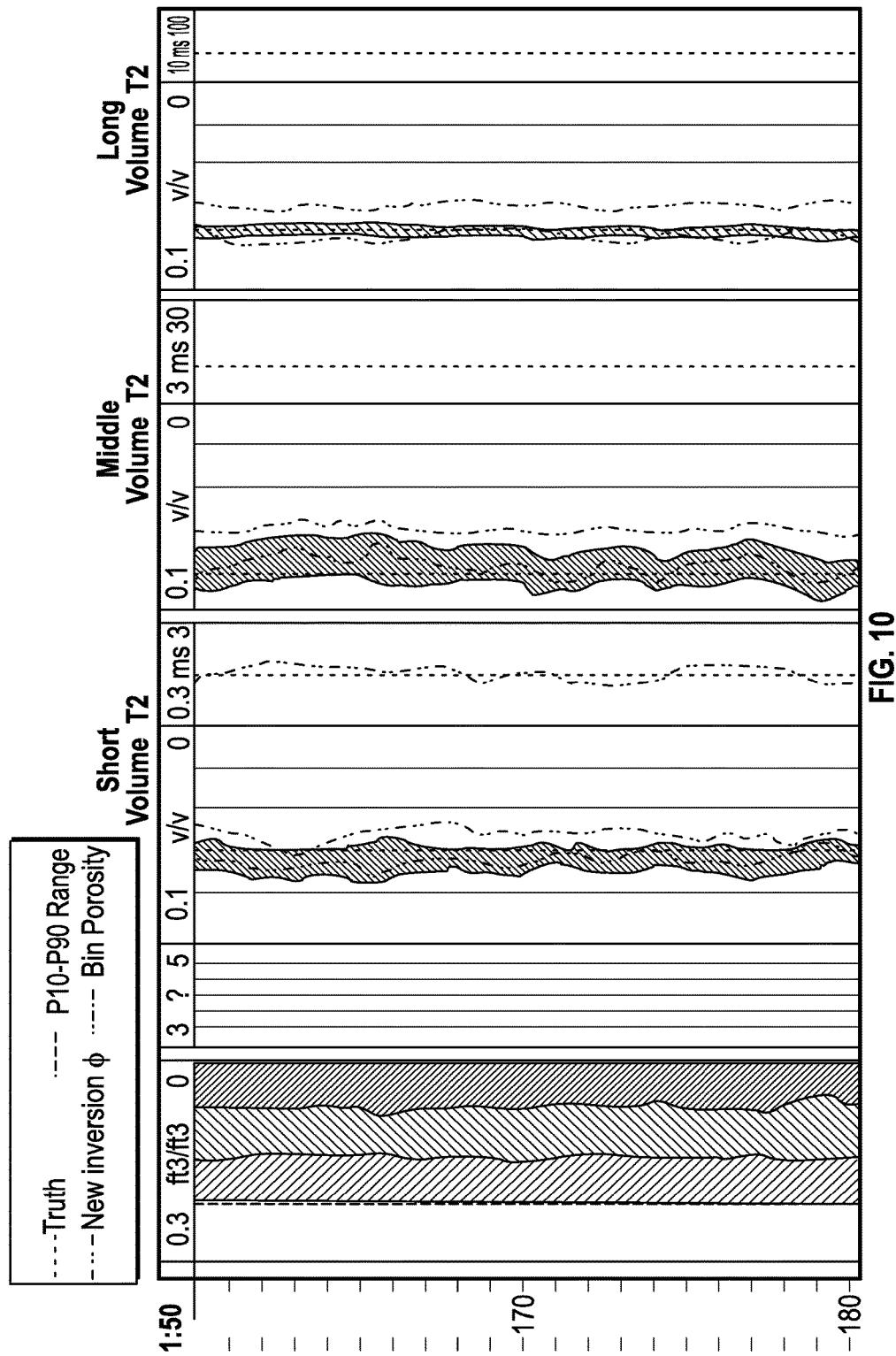
FIG. 10 depicts a graph showing a 0.1 ms short porobodon with 50 bursts, according to an embodiment.
Figure 11:
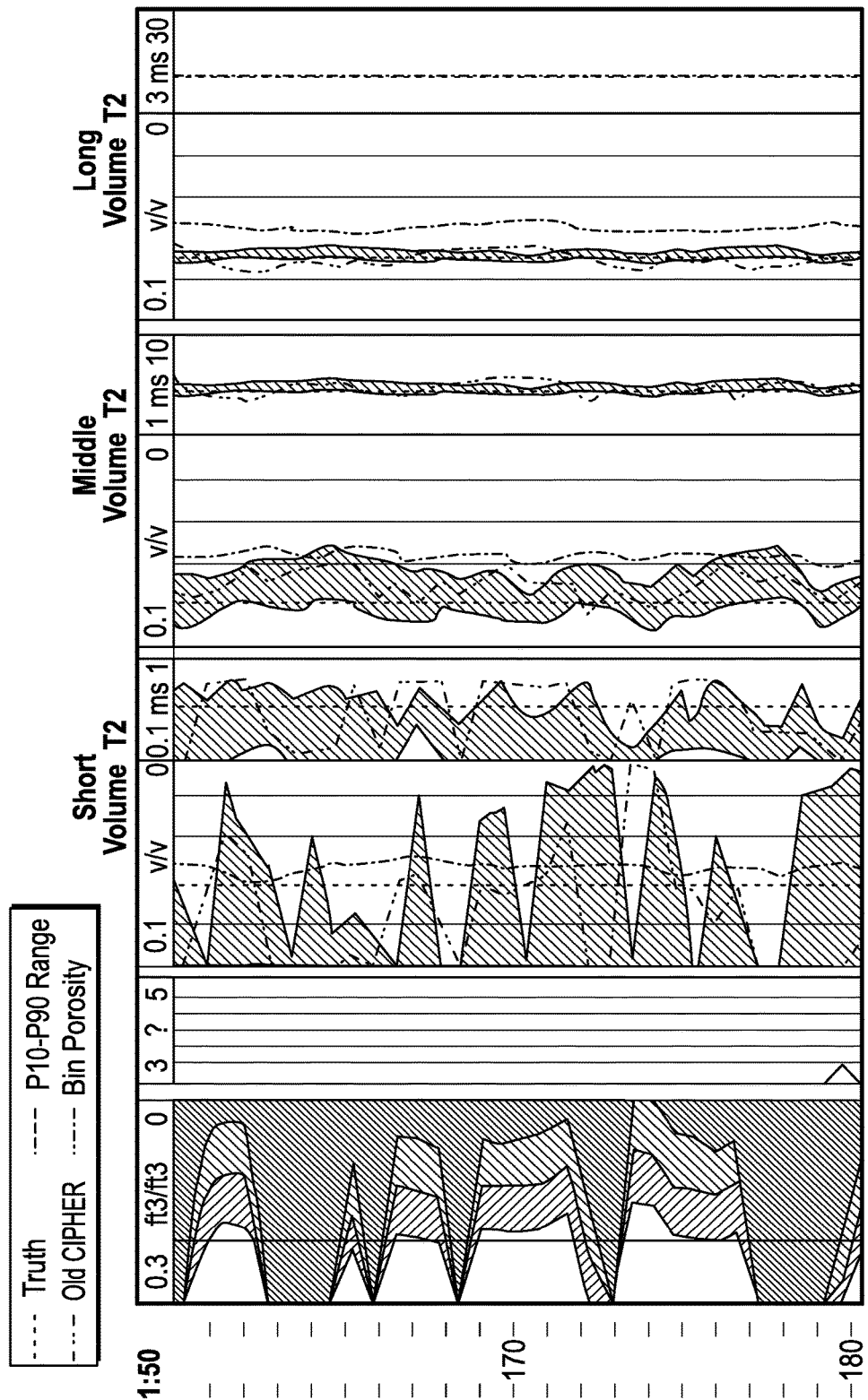
FIG. 11 depicts another graph showing a 0.1 ms short porobodon with 50 bursts, according to an embodiment.

More particularly, FIG. 7 depicts a graph showing a 1 ms short porobodon with 50 bursts. CIPHER$^{SM}$ is shown as stable. FIG. 8 depicts a graph showing a 0.5 ms short porobodon with 50 bursts. CIPHER$^{SM}$ is shown as stable, but inversion accuracy is degraded. FIG. 9 depicts a graph showing a 0.25 ms short porobodon with 50 bursts. CIPHER$^{SM}$ has lost stability at this point. FIG. 10 depicts a graph showing a 0.1 ms short porobodon with 50 bursts. The new inversion is stable. FIG. 11 depicts another graph showing a 0.1 ms short porobodon with 50 bursts. CIPHER$^{SM}$ is shown as unstable.

These figures demonstrate that the new inversion proposed herein is superior with respect to CIPHER$^{SM}$ and to the conventional bin porosity analysis. The new inversion is stable and produces more accurate results even for a case of a 0.1 ms short porobodon while CIPHER$^{SM}$ loses stability for a case of a 0.25 ms short porobodon. Conventional bin porosity volumes are stable for each of the cases; however, they are biased even for the case of 1 ms short porobodon. CIPHER$^{SM}$, if it is stable (1 ms and 0.5 ms short porobodon), delivers superior results compared to bin porosity. The new inversion delivers superior results both compared to CIPHER$^{SM}$ and bin porosity. This happens in spite of the fact that bin porosity analysis was handicapped by using the first echo which was excluded from CIPHER$^{SM}$ and the new inversion. The accuracy of mean T2 porobodon position (T2 in the figures) is quite good for the new inversion. These results demonstrate the applicability of the method disclosed herein for porosity partitioning in a short NMR relaxation range that is characteristic for organic shale containing hydrocarbons.

Figure 12:
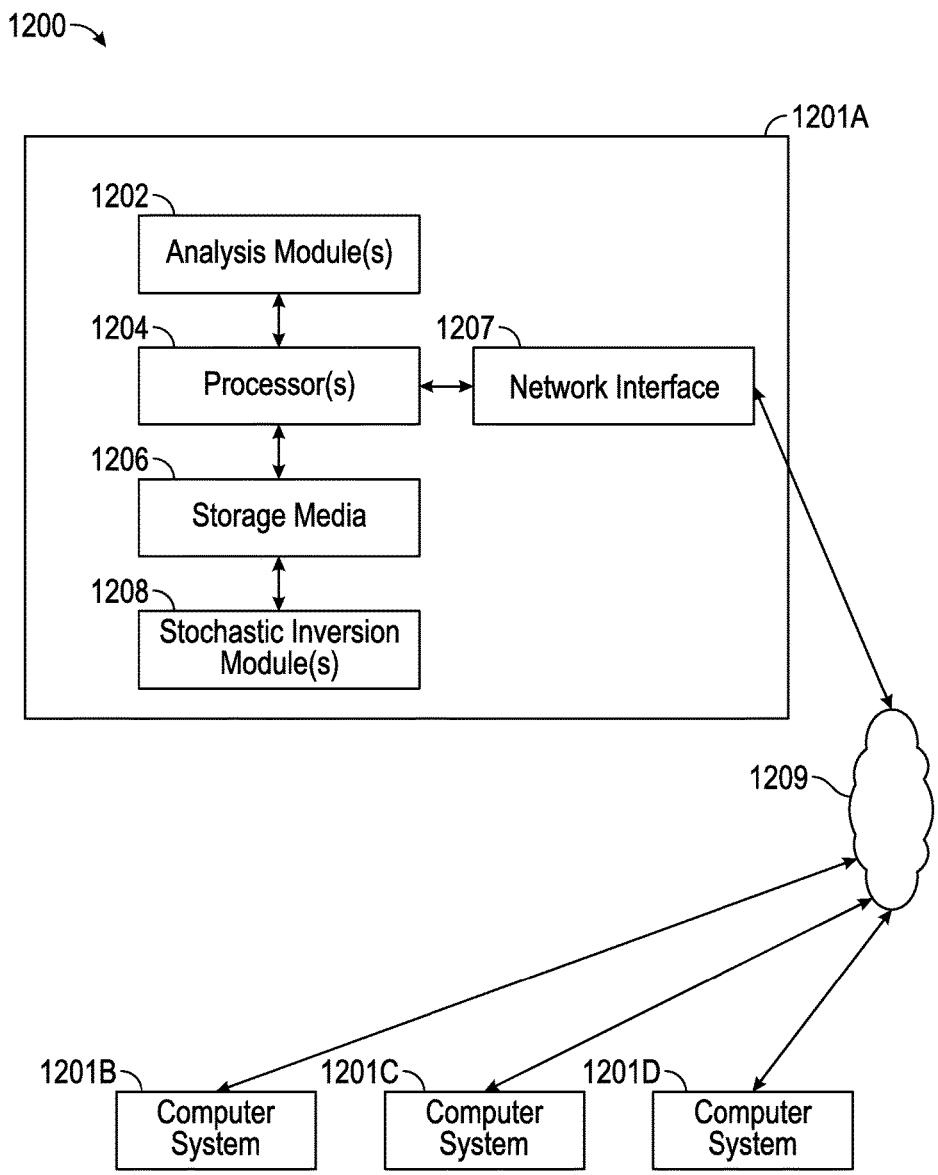
FIG. 12 illustrates a schematic view of a computing or processor system for performing one or more methods disclosed herein, according to an embodiment.

In some embodiments, the methods of the present disclosure may be executed by a computing system. FIG. 12 illustrates an example of such a computing system 1200, in accordance with some embodiments. The computing system 1200 may include a computer or computer system 1201A, which may be an individual computer system 1201A or an arrangement of distributed computer systems. The computer system 1201A includes one or more analysis modules 1202 that are configured to perform various tasks according to some embodiments, such as one or more methods disclosed herein. To perform these various tasks, the analysis module 1202 executes independently, or in coordination with, one or more processors 1204, which is (or are) connected to one or more storage media 1206. The processor(s) 1204 is (or are) also connected to a network interface 1207 to allow the computer system 1201A to communicate over a data network 1209 with one or more additional computer systems and/or computing systems, such as 1201B, 1201C, and/or 1201D (note that computer systems 1201B, 1201C and/or 1201D may or may not share the same architecture as computer system 1201A, and may be located in different physical locations, e.g., computer systems 1201A and 1201B may be located in a processing facility, while in communication with one or more computer systems such as 1201C and/or 1201D that are located in one or more data centers, and/or located in varying countries on different continents).

A processor can include a microprocessor, microcontroller, processor module or subsystem, programmable integrated circuit, programmable gate array, or another control or computing device. The storage media 1206 can be implemented as one or more computer-readable or machine-readable storage media. Note that while in some example embodiments of FIG. 12 storage media 1206 is depicted as within computer system 1201A, in some embodiments, storage media 1206 may be distributed within and/or across multiple internal and/or external enclosures of computing system 1201A and/or additional computing systems. Storage media 1206 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories, magnetic disks such as fixed, floppy and removable disks, other magnetic media including tape, optical media such as compact disks (CDs) or digital video disks (DVDs), BLU-ERAY® disks, or other types of optical storage, or other types of storage devices. Note that the instructions discussed above can be provided on one computer-readable or machine-readable storage medium, or alternatively, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

In some embodiments, computing system 1200 contains one or more stochastic inversion module(s) 1208. In the example of computing system 1200, computer system 1201A includes the stochastic inversion module 1208. In some embodiments, a single stochastic inversion module may be used to perform some or all aspects of one or more embodiments of the methods disclosed herein. In alternate embodiments, a plurality of stochastic inversion modules may be used to perform some or all aspects of methods disclosed herein.

It should be appreciated that computing system 1200 is only one example of a computing system, and that computing system 1200 may have more or fewer components than shown, may combine additional components not depicted in the example embodiment of FIG. 12, and/or computing system 1200 may have a different configuration or arrangement of the components depicted in FIG. 12. The various components shown in FIG. 12 may be implemented in hardware, software, or a combination of both hardware and software, including one or more signal processing and/or application specific integrated circuits.

Further, the steps in the processing methods described herein may be implemented by running one or more functional modules in information processing apparatus such as general purpose processors or application specific chips, such as ASICs, FPGAs, PLDs, or other appropriate devices. These modules, combinations of these modules, and/or their combination with general hardware are all included within the scope of protection of this disclosure.

While the specific embodiments described above have been shown by way of example, it will be appreciated that many modifications and other embodiments will come to the mind of one skilled in the art having the benefit of the teachings presented in the foregoing description and the associated drawings. Accordingly, it is understood that various modifications and embodiments are intended to be included within the scope of the appended claims.

What is claimed is:

1. A method comprising:
receiving, via an interface of a computing system, data representing one or more parameters in a reservoir in an organic shale, wherein the data comprise nuclear magnetic resonance data;
estimating, by stochastically inverting at least a portion of the data with a processor of the computing system, a distribution of porobodon features that matches an observed pulse decay curve of at least a portion of the nuclear magnetic resonance data for pore fluid, wherein the estimating minimizes a difference between at least one porobodon volume and a porosity parameter value; and
based at least in part on the distribution of porobodon features, via the processor, generating a porosity log that characterizes the reservoir in the organic shale.

2. The method of claim 1, wherein the data further comprise elemental capture spectroscopy data.

3. The method of claim 1, further comprising identifying a quantile of a position, a width, or both of the at least one of the porobodon features for use as a restriction boundary.

4. The method of claim 3, further comprising identifying a zone where an additional porobodon feature is present.

5. The method of claim 3, further comprising identifying a zone where two or more additional porobodon features are present, wherein the additional porobodon features are clearly distinct on commercial relaxation time distributions.

6. The method of claim 1, wherein the at least one of the porobodon features comprises a relaxation time that is less than or equal to about 0.25 ms.

7. A non-transitory computer-readable medium comprising instructions executable by at least one processor of a computing system to instruct the computing system to:
receive data representing one or more parameters in a reservoir in an organic shale, wherein the data comprise nuclear magnetic resonance data;
estimate, via stochastic inversion of at least a portion of the data, a distribution of porobodon features that matches an observed pulse decay curve of at least a portion of the nuclear magnetic resonance data for pore fluid, wherein the estimate minimizes a difference between at least one porobodon volume and a porosity parameter value; and
based at least in part on the distribution of porobodon features, generate a porosity log that characterizes the reservoir in the organic shale.

8. The non-transitory computer-readable medium of claim 7, wherein the data comprise elemental capture spectroscopy data.

9. The non-transitory computer-readable medium of claim 7, wherein the instructions further comprise instructions to identify a quantile of a position, a width, or both of the at least one of the porobodon features for use as a restriction boundary.

10. The non-transitory computer-readable medium of claim 9, wherein the instructions further comprise instructions to identify a zone where an additional porobodon feature is present.

11. The non-transitory computer-readable medium of claim 9, wherein the instructions further comprise instructions to identify a zone where two or more additional porobodon features are present, wherein the additional porobodon features are clearly distinct on commercial relaxation time distributions.

12. The non-transitory computer-readable medium of claim 7, wherein the at least one of the porobodon features comprises a relaxation time that is less than or equal to about 0.25 ms.

13. A computing system, comprising:
one or more processors; and
a memory system comprising processor-executable instructions that instruct the computing system to:
receive data representing one or more parameters in a reservoir in an organic shale, wherein the data comprise nuclear magnetic resonance data;
estimate, via stochastic inversion of at least a portion of the data, a distribution of porobodon features that matches an observed pulse decay curve of at least a portion of the nuclear magnetic resonance data for pore fluid, wherein the estimate minimizes a difference between at least one porobodon volume and a porosity parameter value; and
based at least in part on the distribution of porobodon features, generate a porosity log that characterizes the reservoir in the organic shale.

14. The computing system of claim 13, wherein the data comprise elemental capture spectroscopy data.

15. The computing system of claim 13, wherein the instructions further comprise instructions to identify a quantile of a position, a width, or both of the at least one of the porobodon features for use as a restriction boundary.

16. The computing system of claim 15, wherein the instructions further comprise instructions to identify a zone where an additional porobodon feature is present.

17. The computing system of claim 13, wherein the instructions further comprise instructions to identify a zone where two or more additional porobodon features are present, wherein the additional porobodon features are clearly distinct on commercial relaxation time distributions.

18. The computing system of claim 13, wherein the at least one of the porobodon features comprises a relaxation time that is less than or equal to about 0.25 ms.

19. The method of claim 1 wherein the estimating minimizes a sum of a plurality of porobodon volumes and the porosity parameter value.

* * * * *